United States Patent [19]
Winter

[11] Patent Number: 5,114,405
[45] Date of Patent: May 19, 1992

[54] SINGLE USE TAMPER RESISTANT SYRINGE

[76] Inventor: Douglas A. Winter, 160 Parkwood Rd., West Islip, N.Y. 11795

[21] Appl. No.: 525,833

[22] Filed: May 21, 1990

[51] Int. Cl.$^5$ .............................................. A61M 5/00
[52] U.S. Cl. .................................. 604/110; 604/218; 604/220
[58] Field of Search ............... 604/110, 218, 220, 187, 604/207, 208, 210

[56] References Cited

U.S. PATENT DOCUMENTS

| | | | |
|---|---|---|---|
| 4,391,272 | 7/1983 | Staempfli | 604/110 |
| 4,747,830 | 5/1988 | Gloyer et al. | 604/110 |
| 4,820,272 | 4/1989 | Palmer | 604/110 |
| 4,840,616 | 6/1989 | Banks | 604/110 |
| 4,932,941 | 6/1990 | Min et al. | 604/110 |
| 4,995,869 | 2/1991 | McCarthy | 604/220 X |

FOREIGN PATENT DOCUMENTS

| | | | |
|---|---|---|---|
| 2621824 | 4/1989 | France | 604/110 |
| 2197792 | 6/1988 | United Kingdom | 604/110 |

Primary Examiner—John D. Yasko
Attorney, Agent, or Firm—Galgano & Belkin

[57] ABSTRACT

A single use tamper resistant syringe having a locking member which prevents retraction of the plunger after the latter has been fully depressed and discharging the contents of the syringe. The proximal end of the plunger is provided with an abutment and the inside of the barrel is provided with dogs which are biased inwardly. When the plunger is depressed and the abutment slides by the dogs the latter extend into the barrel to block retraction of the plunger. Tampering of the locking arrangement prior to use of the syringe is prevented by providing a detachable piston cap at the distal end of the plunger so that when the plunger is removed prior to use the cap is dislodged by said dogs and remains within the barrel of the syringe thereby rendering inoperative the syringe.

1 Claim, 2 Drawing Sheets

SINGLE USE TAMPER RESISTANT SYRINGE

BACKGROUND OF THE INVENTION

The present invention relates to a single use tamper resistant syringe and more particularly to a syringe which becomes inoperable after a single use.

One of the ways that the AIDS virus, herpes, and certain other highly communicable diseases are transmitted is through the sharing of a needle by drug users. The syringe is utilized by one user and then is passed on to another user who refills the syringe and uses the needle again.

Attempts have been made to discourage the multiple use of a syringe by offering free syringes to drug users. This has not been effective to slow down the multiple use of needles because of the reluctance of drug users to come forth and expose themselves by requesting the needles.

SUMMARY OF THE INVENTION

In this invention the sharing of syringes with needles is avoided by a syringe design which makes it virtually impossible to employ a syringe after one use and is also difficult to tamper with.

A preferred embodiment of this invention consists of a syringe having a plunger and a locking device which prevents the plunger from being retracted after use. Another feature is designed to inhibit the avoidance of the locking arrangement.

It is thus a principal object of this invention to provide a syringe which is incapable of more than a single use and is tamper resistant.

Other objects and advantages of this invention will hereinafter become obvious from the following detailed description of a preferred embodiment of this invention.

DESCRIPTION OF THE PREFERRED EMBODIMENTS

Figure 1:
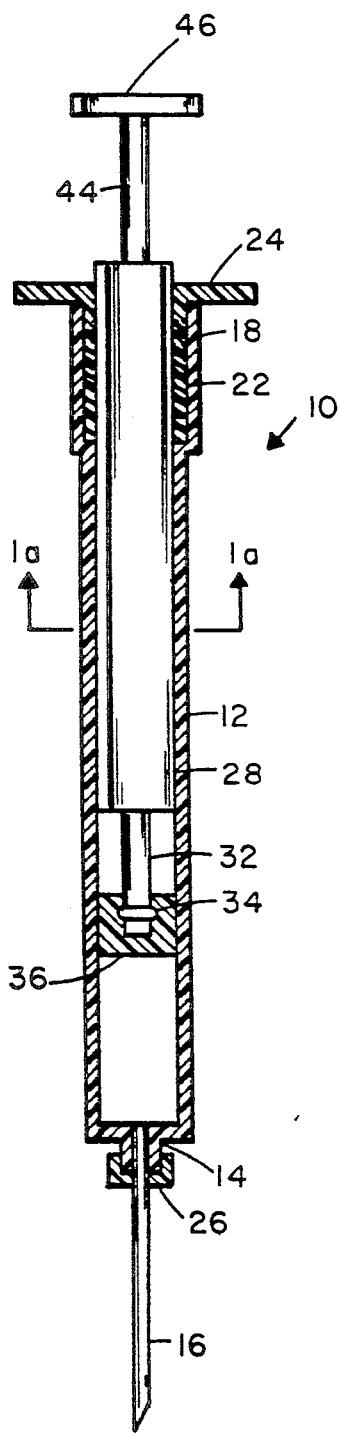
FIG. 1 is an elevation view in section showing a preferred embodiment of this invention ready for use.

Referring to FIG. 1, there is shown syringe 10 comprising a hollow cylindrical barrel 12 with a lower extension 14 at the distal end to which is integrally attached to a hollow needle 16 of metal construction.

The upper portion or proximal end of barrel 12 is provided with an expanded section 18 to accommodate a lock 2 and upper barrel cap 24 both of which will be described in greater detail. A lower barrel cap 26 closes off lower extension 14 and permits needle 16 to pass therethrough.

Figure 1A:
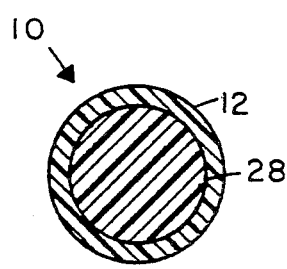
FIG. 1a is a section taken along 1a-1a of FIG. 1.
Figure 2:
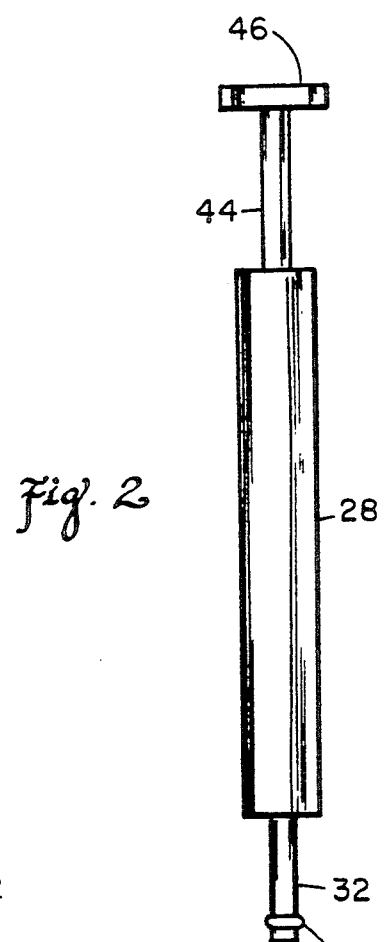
FIG. 2 is an elevation view of the plunger.
Figure 3:
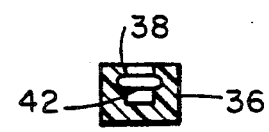
FIG. 3 is a section view of the plunger cap.

Within barrel 12 is a slidable plunger 28 details of which are shown in FIGS. 1a, 2, and 3. Plunger 28 is a solid member circular in cross section with a lower extension 32 with an annular ridge 34 adjacent the tip of extension 32. Mounted over the tip of extension 32 is a cylindrical cap 36 having an opening 38 and an annular groove 42 to snap onto and engage ridge 34 as seen in FIG. 1. The bottom face of cap 36 acts as the piston surface within barrel 12.

Figure 4:
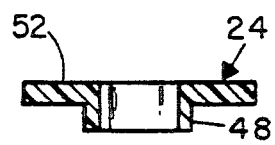
FIG. 4 is a section view of the upper barrel cap.

The upper end of plunger 28 is provided with a neck 44 terminating in a thumb depressor 46. When mounted within barrel 12, annular sleeve 48 having a collar 52 making up upper barrel cap 24 (as seen in FIG. 4) is inserted as illustrated in FIG. 1 to provide a place where fingers may be placed in order to press down on thumb depressor 46 as is understood in the art. Also, as noted earlier, cap 24 in place secures lock 22.

Figure 5:
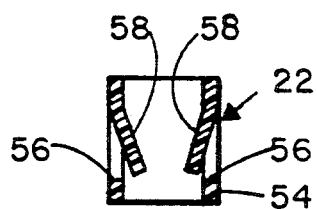
FIG. 5 is a section view of the plunger lock.
Figure 6:
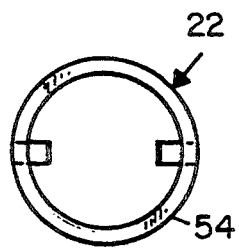
FIG. 6 is an end view of the plunger lock.

As seen in FIGS. 5 and 6, lock 22 consists of a hollow, circular cylinder 54 with a pair of oppositely facing openings 56 formed by a pair of dogs 58 cut out of cylinder 54 and biased inwardly as illustrated in FIG. 5.

In the operation of syringe 10, the latter is delivered and ready for use in the condition illustrated in FIG. 1. Plunger cap 36 comes mounted on plunger extension 32. In lock 22, dogs 58 are spread into openings 56 by the outer surface of plunger 28 so that the latter is freely slidable.

By retracting plunger 28 upwardly the liquid to be delivered by way of syringe 10 is drawn in through needle 16 as is understood in the art and the air present within barrel is removed by inverting syringe 10 and pressing plunger 28 forwardly until the liquid begins to come out of needle 16, as is understood in the art.

Figure 7:
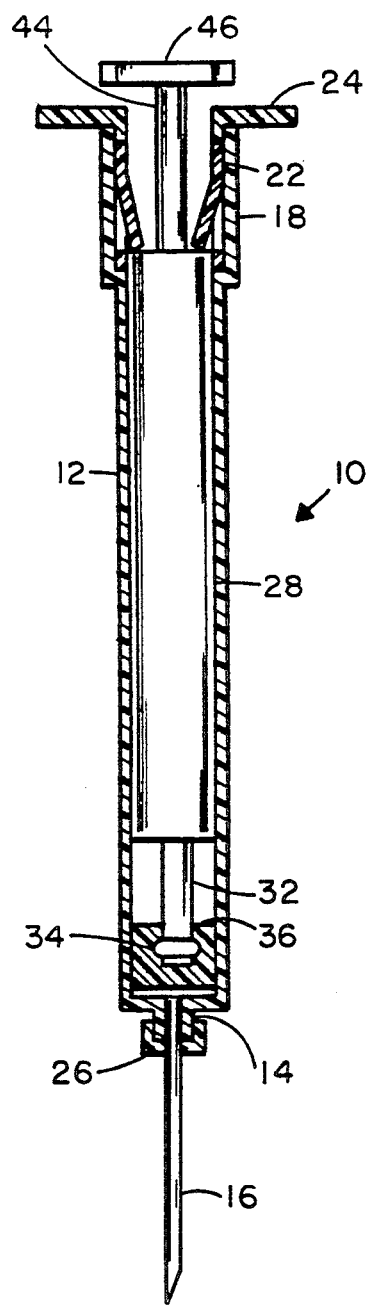
FIG. 7 is a view similar to that of FIG. 1 of the syringe after use.

When plunger 28 is depressed completely as seen in FIG. 7 to deliver through needle 16 all of the contents of barrel 12, dogs 58 will clear the upper edges of the solid portion of plunger 28 and effectively block the retraction of plunger 28. This action will effectively prevent syringe 10 from being used again.

It would be difficult if not impossible to render ineffective the blocking action of lock 22 without destroying the syringe itself. However, since it is not impossible to defeat the described blocking action, syringe 10 is described as being tamper resistant rather than tamper proof.

Figure 8:
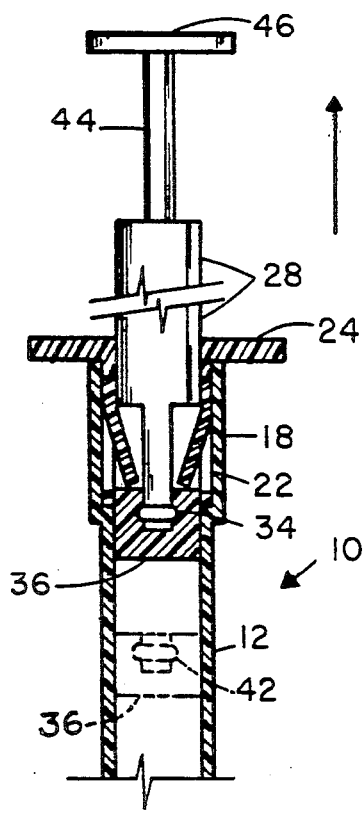
FIG. 8 is an elevation view in section of the upper portion of the embodiment of FIG. 1 showing the operation of the lock to prevent tampering.

Under some circumstances the user of syringe 10 might attempt to defeat the operation of lock 22 before the syringe is put to use. This conceivably could be accomplished by first removing plunger 28 from barrel 12. If the user attempts this, dogs 58 will dislodge plunger cap 36 from lower extension 32 of plunger 28 as seen in FIG. 8, causing cap 36 to remain within barrel 12 as shown in phantom and rendering syringe 10 totally useless.

In this invention as described it is seen that there has been provided a needle which is incapable of reuse under normal circumstances and is resistant to any tampering which would permit multiple use.

While only one embodiment of the invention has been described it is understood that many variations are possible without departing from the principles of this invention as defined in the claims which follow.

What is claimed is:

1. A single use syringe comprising:
   a. hollow cylindrical barrel means containing plunger means having an abutment adjacent the proximal end of said plunger means within said barrel means when said plunger means is fully depressed and slidable within said barrel means;
   b. said hollow cylindrical barrel means having hollow needle means extending from the distal end of and communicating with the interior of said barrel means;

c. said plunger means extending out of the proximal end of said barrel means;

d. lock means comprising a dog mounted within and adjacent the proximal end of said barrel means for engaging said abutment when the plunger means is fully depressed within said barrel means after delivering the contents of said syringe through said needle to prevent retraction and reuse of said syringe, said dog being biased in the direction of said abutment, said plunger means having a cylindrical body forming said abutment at one end and extending toward the distal end of said syringe, said cylindrical body preventing said dog from engaging said abutment until said plunger means is fully depressed within said barrel means, the distal end of said plunger means including detachable plunger cap means forming the piston end of said plunger means for ejecting fluid out of said syringe through said needle means when said plunger means is depressed, and said detachable plunger cap means including an abutment for engagement by said dog when said plunger means is withdrawn from said barrel means prior to use of said syringe to dislodge said plunger cap means from said plunger means thereby rendering ineffective said syringe to prevent tampering of said lock means within said barrel means.

* * * * *